United States Patent [19]

Durant et al.

[11] 4,105,770

[45] Aug. 8, 1978

[54] HETEROCYCLOMETHYLSULPHINYLETHYL DERIVATIVES OF N-CYANOGUANIDINES, THIOUREAS AND 2-AMINO-1-NITROETHYLENE

[75] Inventors: Graham John Durant; Charon Robin Ganellin, both of Welwyn Garden City, England; Torben Hesselbo, North Berwick, Scotland; George Raymond White, Harpenden, England

[73] Assignee: Smith Kline & French Laboratories Limited, Welwyn Garden City, England

[21] Appl. No.: 787,245

[22] Filed: Apr. 13, 1977

Related U.S. Application Data

[62] Division of Ser. No. 704,871, Jul. 13, 1976, Pat. No. 4,038,408.

[30] Foreign Application Priority Data

Jul. 31, 1975 [GB] United Kingdom ............... 31969/75

[51] Int. Cl.$^2$ .................. C07D 417/02; C07D 403/02; A61K 31/44

[52] U.S. Cl. ........................... 424/263; 260/294.8 D; 260/294.8 F; 260/294.8 H; 548/336; 424/273 R

[58] Field of Search ................ 260/294.8 D, 294.8 F, 260/294.8 H; 548/336; 424/273 R, 263

[56] References Cited

U.S. PATENT DOCUMENTS

| 3,968,227 | 7/1976 | Durant et al. ............... 260/294.8 G |
| 3,979,398 | 9/1976 | White ............................ 260/294.8 F |
| 4,025,527 | 5/1977 | Durant et al. .................. 260/302 H |

*Primary Examiner*—Alan L. Rotman
*Attorney, Agent, or Firm*—Joan S. Keps; Richard D. Foggio; William H. Edgerton

[57] ABSTRACT

The compounds are heterocyclomethylsulphinylethyl derivatives of N-cyanoguanidines, thioureas and 2-amino-1-nitroethylene which are histamine $H_2$-antagonists or are converted into histamine $H_2$-antagonists in the animal body. Two specific compounds of the present invention are 1-nitro-2-[2-((2-thiazolyl)methylsulphinyl)ethylamino]-2-[2-((2-thiazolyl)methylthio)ethylamino]ethylene and 1-nitro-2,2-bis-[2-((2-thiazolyl)methylsulphinyl)ethylamino]ethylene.

10 Claims, No Drawings

HETEROCYCLOMETHYLSULPHINYLETHYL DERIVATIVES OF N-CYANOGUANIDINES, THIOUREAS AND 2-AMINO-1-NITROETHYLENE

This is a division of application Ser. No. 704,871 filed July 13, 1976 now U.S. Pat. No. 4,038,408 filed July 26, 1977.

This invention relates to pharmacologically active compounds, to pharmaceutical compositions containing these compounds and to methods of blocking histamine $H_2$-receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines," of which mepyramine, diphenhydramine and chlorpheniramine are typical examples, are mediated through histamine $H_1$-receptors (Ash and Schild, Brit. J. Pharmac. Chemother, 27, 427, (1966)). However, other of the biological actions of histamine are not inhibited by "antihistamines" and actions of this type which are inhibited by a compound described by Black et al. (Nature, 236, 385 (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines." Histamine $H_2$-antagonists are therefore useful, for example, as inhibitors of gastric acid secretion, as anti-inflammatory agents and as agents which act on the cardiovascular system, for example as inhibitors of the effects of histamine on blood pressure. In the treatment of certain conditions, for example inflammation and in inhibiting the actions of histamine on blood pressure, a combination of histamine $H_1$- and $H_2$-antagonists is useful.

The compounds of this invention are histamine $H_2$-antagonists. In U.S. Pat. No. 3,932,443, sulphoxides of Formula 1 are disclosed:

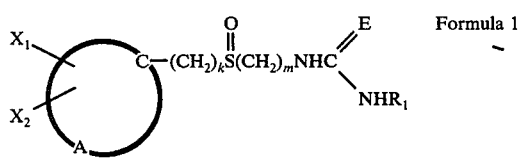

FORMULA 1 wherein A is such that there is formed with the carbon atom shown an unsaturated heterocyclic nucleus, preferably having five or six atoms, which nucleus comprises at least one nitrogen atom and may comprise further hereto atoms such as sulphur and oxygen, e.g., imidazole, pyridine, thiazole, isothiazole, oxazole, isoxazole, pyrazole, triazole, thiadiazole, pyrimidine, pyrazine or pyridazine; $X_1$ and $X_2$ which may be the same or different are hydrogen, lower alkyl, trifluoromethyl, hydroxyl, halogen, amino, or $X_1$ may with $X_2$ and at least two of the atoms comprising A form a further ring, e.g., a benzene ring, a pyrimidine ring or a partially unsaturated ring; $k$ is 0 to 2 and $m$ is 2 or 3 provided that the sum of $k$ and $m$ is 3 or 4; E is oxygen, sulphur or $NR_2$; $R_1$ is hydrogen, lower alkyl such as methyl, acyl, e.g., benzoyl or dialkylaminoalkyl, e.g., dimethylaminoethyl; and $R_2$ is hydrogen, nitro, cyano, alkanesulphonyl or arenesulphonyl.

We have now found that certain other sulphoxide compounds not covered by Formula 1 are useful in the inhibition of histamine $H_2$-receptors in the animal body and it is to these compounds that the present invention relates.

Accordingly we provide compounds of the following Formula 2:

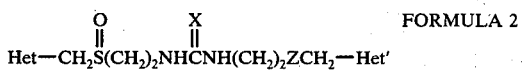

FORMULA 2

FORMULA 2 wherein Het and Het' are each selected from imidazole optionally substituted by methyl or bromo, pyridine optionally substituted by methoxy, hydroxy, chlorine or bromine, thiazole and isothiazole; Z is sulphur, SO or methylene and X is sulphur, $CHNO_2$ or NCN, or a pharmaceutically acceptable acid addition salt thereof.

Throughout the present specification, by the terms "lower alkyl" and "lower alkoxy" we mean alkyl and alkoxy groups containing from 1 to 4 carbon atoms. It will be understood that the structure illustrated in Formula 2 is only one of several possible representations and that other tautomeric forms are also covered by the present invention. Hydrates, pharmaceutically acceptable salts and hydrated pharmaceutically acceptable salts of compounds of Formula 2 are also covered by the present invention.

Preferably Het and Het' are selected from 5-methyl-4-imidazolyl, 5-bromo-4-imidazolyl, 3-methoxy-2-pyridyl, 3-hydroxy-2-pyridyl, 3-chloro-2-pyridyl, 3-bromo-2-pyridyl, 2-thiazolyl and 3-isothiazolyl.

Preferably Het and Het' are identical.
Preferably Z is sulphur.
Preferably X is $CHNO_2$ or NCN.

Specific compounds within the scope of the present invention are: 1-nitro-2-[2-((2-thiazolyl)methylsulphinyl)ethylamino]-2-[2-((2-thiazolyl)methylthio)ethylamino]ethylene and 1-nitro-2,2-bis-[2-((2-thiazolyl)methylsulphinyl)ethylamino]-ethylene.

The compounds of the present invention may be produced by a process which comprises the step of treating a compound of the Formula 3:

FORMULA 3 wherein Het has the same significance as in Formula 2 and Q is hydrogen or, when X is $CHNO_2$ or NCN, $—CX.NH(CH_2)_2ZCH_2—$ Het' (where Het' and Z have the same significance as in Formula 2) with a suitable oxidising agent. Suitable oxidising agents include peroxybenzoic acid, substituted peroxybenzoic acids such as m-chloroperoxybenzoic acid, peroxyacetic acid and periodates (metaperiodates) such as sodium metaperiodate. A preferred oxidising agent is sodium metaperiodate. We have found that hydrogen peroxide is not a suitable oxidising agent for the preparation of compounds of Formula 2 wherein X is sulphur.

Preferably the oxidation is carried out in water or an aqueous solution of a water-miscible polar solvent, such as aqueous acetone.

Preferably the oxidation is carried out at between 0° and 30° C.

Preferably compounds of Formula 2 wherein Z is sulphur are prepared by oxidising a compound of Formula 3 wherein Q is hydrogen, and converting this aminesulphoxide into a compound of Formula 2 by one of the methods described below. Compounds of Formula 2 wherein Z is sulphur and Het and Het' are identical may be prepared by oxidising a compound of Formula 3 wherein Q is —CXNH(CH$_2$)$_2$SCH$_2$Het' under controlled conditions, e.g., using only one equivalent of oxidising agent. Conversely, when it is required to produce the compound having two sulphoxide groups this restriction will not of course be necessary and 2 equivalents of oxidising agent may be used.

When Q is hydrogen the product of this oxidation is an aminesulphoxide of Formula 4:

FORMULA 4 wherein Het has the same significance as in Formula 2, and this aminesulphoxide may be converted into a compound of Formula 2 by one of the following series of reactions (outlined in Scheme 1):

oureas of Formula 5 wherein X is sulphur may be prepared by treatment of an amine of Formula 6 with carbon disulphide and subsequent alkylation, and the isothioureas of Formula 5 wherein X is NCN or CHNO$_2$ may be prepared by treating a compound XC(SA)$_2$ with one equivalent of an amine of Formula 6.

(b) When X is sulphur the aminesulphoxide of Formula 4 may be treated with carbon disulphide, and the resultant dithiocarbamate alkylated and treated with an amine of Formula 6:

H$_2$N(CH$_2$)$_2$ZCH$_2$Het'

FORMULA 6 wherein Z and Het' have the same significance as in Formula 2, to give a compound of Formula 2.

(c) When X is CHNO$_2$ or NCN the aminesulphoxide of Formula 4 may be treated under suitable conditions with a compound of formula (AS)$_2$C=X wherein A is lower alkyl, preferably methyl, to give a compound of Formula 7 (see scheme 1) which is treated with an amine of Formula 6 to give a compound of Formula 2.

(d) When X is CHNO$_2$ the amine sulphoxide of Formula 4 may be treated with 1-alkylsulphinyl-1-alkylthio-2-nitroethylene to give a compound of Formula 7, which is subsequently treated with an amine of Formula 6 to give a compound of Formula 2.

The starting materials of Formula 3 wherein Q is —CX.NH(CH$_2$)$_2$ZCH$_2$—Het' may be prepared by the general methods outlined above and in Scheme 1 for converting an aminesulphoxide of Formula 4 into a compound of Formula 2 (by substituting and aminethioether for the aminesulphoxide of Formula 4).

SCHEME 1

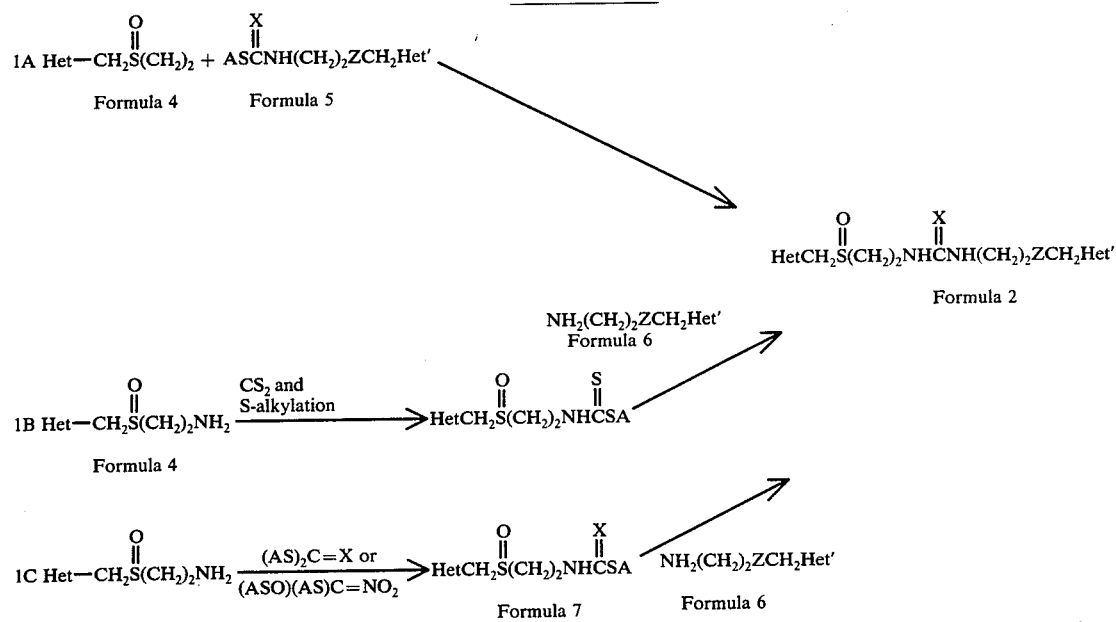

(a) The aminesulphoxide of Formula 4 may be treated with an isothiourea of Formula 5.

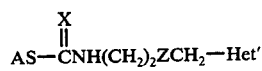

FORMULA 5 wherein Het', Z and X have the same significance as in Formula 2 and A is lower alkyl, such as methyl. Isothi- The sulphoxides of the present invention find their utility in the inhibition of histamine H$_2$-receptors in the animal body. Although we do not wish to be limited in any way by the following explanation of this utility, we believe that this is partly due to the metabolic reductive conversion of the sulphoxides to the corresponding thioether compounds which are potent histamine H$_2$-receptor antagonists. This conversion is thought to occur in the large intestine of the animal where the active reducing agent is probably present in the intestinal bacterial flora. Because of this mechanism and the differing partition coefficients of the sulphoxides and the corresponding thioethers the principal histamine H₂-receptor antagonism action may be delayed for a considerable time after the administration of the sulphoxides. This is a particularly useful effect in many cases and may be utilised, for example to provide a continuing supply of antagonist to an animal after the effect of an initial dose of a thioether compound has started to decline. In this regard it is of course possible to administer the sulphoxides of the present invention at the same time and possibly in combination with the said initial dose.

In addition to the above, certain of the sulphoxides of the present invention, in particular those sulphoxides of Formula 2 wherein Z is sulphur or methylene, have intrinsic activity as histamine H₂-antagonists and for example have been found to inhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash and Schild. The activity of these compounds as histamine H₂-antagonists is also demonstrated by their ability to inhibit other actions of histamine which, according to the above mentioned paper of Ash and Schild, are not mediated by histamine H₁-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention with intrinsic acitivity show antiinflammatory activity in conventional tests such as the rat paw oedema test, where the oedema is induced by an irritant. The rat paw volume is reduced by subcutaneous injection of doses of about 500 micromoles/Kg of a compound of Formula 2 wherein Z is sulphur or methylene. In a conventional test, such as the measurement of blood pressure in the anaesthetised rat, the action of the compounds of this invention in inhibiting the vasodilator action of histamine can also be demonstrated.

The level of activity of the compounds of this invention is illustrated by the effective dose producing 50% inhibition of gastric acid secretion in the anaesthetised rat and the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula 2 or a pharmaceutically acceptable acid addition salt thereof and methods of blocking histamine H₂-receptors which comprise administering to an animal a compound of Formula 2 or a pharmaceutically acceptable acid addition salt thereof are also objects of this invention. The pharmaceutical carrier employed may be, for example, either a solid or liquid. Examplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, an aqueous or nonaqueous liquid suspension and for compounds of Formula 2 wherein Z is S or CH₂ as a sterile injectable liquid contained for example in an ampoule.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine H₂-receptors in an animal body. The route of administration may be oral or in the case of compounds of Formula 2 wherein Z is S or CH₂, parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration, for example as a tablet, capsule, injectable solution or as a cream or ointment for topical application.

The invention is illustrated but in no way limited by the following Examples:

EXAMPLE 1

1-Nitro-2-[2-(2-thiazolylmethylthio)ethylamino]-2-[2-(2-thiazolylmethylsulphinyl)ethylamino]ethylene 1-Nitro-2,2-bis-[2-(2-thiazolylmethylthio)ethylamino]ethylene (4.5 g) was added to a stirred solution of an equivalent amount of sodium methaperiodate (2.3 g) in water (1600 ml), and the resulting solution was stirred at room temperature for 20 hours. Evaporation of the solvent and chromatographic purification of the residue on silica gel gave the title product as an oil. The structure of the product was confirmed by the 100 mHz n.m.r. spectrum in $^2H_6$-dimethylsulphoxide which showed the following resonances:

| thiazole-4-H | quartet at δ7.88,δ7.70) | integral 4.0 protons |
| --- | --- | --- |
| thiazole-5-H | δ7.75 and δ7.59 | (standard) theory 4.0 protons. |
| =CHNO₂ | singlet at δ6.59 | integral 0.9 protons theory 1 proton |
| thiazole-CH₂—SO | quartet at δ4.65 and δ4.55 | integral 1.7 protons theory 2 protons |
| thiazole-CH₂—S | singlet at δ4.17 | integral 0.9 pro- |

-continued

| | | tons |
|---|---|---|
| CH$_2$N | multiplet at δ3.7 | theory 1 proton<br>integral 3.8 protons |
| CH$_2$N | multiplet at δ3.5 | theory 4 protons |
| SOCH$_2$CH$_2$ | multiplet at δ3.1 | integral 1.9 protons<br>theory 2 protons |
| SCH$_2$CH$_2$ | triplet at δ2.7 | integral 2.0 protons<br>theory 2 protons |

EXAMPLE 2

1-Nitro-2,2-bis-[2-(2-thiazolylmethylsulphinyl)ethylamino]ethylene

1-Nitro-2,2-bis-[2-(2-thiazolylmethylthio)ethylamino]ethylene (4.8 g) was added to a stirred solution of sodium metaperiodate (4.58 g) in water (1500 ml) and the mixture was stirred at room temperature for 24 hours. The mixture was concentrated under reduced pressure and was extracted with chloroform and n-octanol and the aqueous solution was evaporated to a solid which was purified by thick layer chromatography on silica gel, eluting with chloroform/ methanol 5:1 to give the title product. The 100 mHz n.m.r. spectrum of the product in $^2$H$_6$-dimethylsulphoxide/deuteriochloroform showed the following resonances:

| thiazole-4-H | AB quartet at δ7.87 and<br>and δ7.56) | integral 4.3 protons<br>theory 4 protons |
|---|---|---|
| thiazole-5-H | | |
| =CHNO$_2$ | singlet at δ6.67 | integral 1.0 protons<br>theory 1 proton |
| thiazole-CH$_2$—SO | AB quartet at δ4.67<br>δ4.50 | integral 4.0 protons (reference<br>theory 4 protons |
| CH$_2$N + HDO | multiplet at δ3.7 | integral 8.6 protons<br>theory 4 protons |
| SOCH$_2$—CH$_2$ | multiplet at δ3.1 | integral 4.2 protons<br>theory 4 protons |

It was particularly observed that the spectrum contained no peaks corresponding to the thiazole—CH$_2$—S— or S—CH$_2$ peaks found in the spectrum of the mono-sulphinyl product of Example 1.

EXAMPLE 3

When the following compounds (a) N-cyano-N',N''-bis-[2-((5-methyl-4-imidazolyl)methylthio)ethyl]guanidine,
(b) N-cyano-N',N''-bis-[2-((5-bromo-4-imidazolyl)methylthio)ethyl]guanidine,
(c) N-cyano-N',N''-bis-[2-((3-bromo-2-pyridyl)methylthio)ethyl]guanidine,
(d) N-cyano-N',N''-bis-[2-(2-pyridylmethylthio)ethyl]guanidine,
(e) N-cyano-N',N'-bis-[2-(2-thiazolylmethylthio)ethyl]guanidine,
(f) 1-nitro-2,2-bis[2-((3-isothiazolyl)methylthio)ethylamino]ethylene, are substituted for 1-nitro-2,2-bis-[2-(2-thiazolylmethylthio)ethylamino]ethylene in the general procedure of Example 1 the following compounds are produced:

(a) N-cyano-N'-[2-((5-methyl-4-imidazolyl)methylthio)ethyl]-N''-[2-((5-methyl-4-imidazolyl)methylsulphinyl)ethyl]guanidine,
(b) N-cyano-N'-[2-((5-bromo-4-imidazolyl)methylthio)ethyl]-N''-[2-((5-bromo-4-imidazolyl)methylsulphinyl)ethyl]guanidine,
(c) N-cyano-N'-[2-((3-bromo-2-pyridyl)methylthio)ethyl]-N''-[2-((3-bromo-2-pyridyl)methylsulphinylethyl]guanidine,
(d) N-cyano-N'-[2-(2-pyridylmethylthio)ethyl]-N''-[2-(2-pyridylmethylsulphinyl)ethyl]guanidine,
(e) N-cyano-N'-[2-(2-thiazolylmethylthio)ethyl]-N''-[2-(2-thiazolylmethylsulphinyl)ethyl]guanidine,
(f) 1-nitro-2-[2-(3-isothiazolylmethylthio)ethylamino]-2-[2-(3-isothiazolylmethylsulphinyl)ethylamino]guanidines.

Oxidation of the same starting materials by the procedure of Example 2 with two equivalents of sodium metaperiodate yields the corresponding bis sulphinyl guanidine.

EXAMPLE 4

Oxidation of one portion the following compounds with one equivalent of sodium metaperiodate:

(a) 3-methoxy-2-(2-aminoethylthio)methylpyridine,
(b) 3-hydroxy-2-(2-aminoethylthio)methylpyridine,
(c) 3-chloro-2-(2-aminoethylthio)methylpyridine,;
(d) 5-bromo-4-(2-aminoethylthio)methylimidazole, yields the corresponding (2-aminoethylsulphinyl)methyl compounds.

Reaction of a second portion of the same starting materials with 1-methylthio-1-methylsulphinyl-2-nitroethylene yields respectively:

(a) 1-methylthio-2-nitro-1-[2-((3-methoxy-2-pyridyl)methylthio)ethylamino]ethylene,
(b) 1-methylthio-2-nitro-1-[2-((3-hydroxy-2-pyridyl)methylthio)ethylamino]ethylene,
(c) 1-methylthio-2-nitro-1-[2-((3-chloro-2-pyridyl)methylthio)ethylamino]ethylene and
(d) 1-methylthio-2-nitro-1-[2-((5-bromo-4-imidazolyl)methylthio)ethylamino]ethylene and treatment of these compounds with the corresponding (2-aminoethylsulphinyl)methyl compounds prepared above, the products are respectively:

(a) 1-nitro-2-[2-((3-methoxy-2-pyridyl)methylthio)ethylamino]-2-[2-((3-methoxy-2-pyridyl)methylsulphinyl)ethylamino]ethylene,
(b) 1nitro-2-[2-((3-hydroxy-2-pyridyl)methylthio)ethylamino]-2-[2-((3-hydroxy-2-pyridyl)methylsulphinyl)ethylamino]ethylene,
(c) 1-nitro-2-[2-((3-chloro-2-pyridyl)methylthio)ethylamino]-2-[2-((3-chloro-2-pyridyl)methylsulphinyl)ethylamino]ethylene and
(d) 1-nitro-2-[2-((5-bromo-4-imidazolyl)methylthio)ethylamino]-2-[2-((5-bromo-4-imidazolyl)methylsulphinyl)ethylamino]ethylene.

EXAMPLE 5

Reaction of 3-methoxy-2-(2-aminoethylsulphinylmethyl)pyridine with 1-methylthio-1methylsulphinyl-2-nitroethylene yields 1-methylthio-2-nitro-1-[2-((3-methoxy-2-pyridyl)methylsulphinyl)ethylamino]ethylene which, when reacted with 4-(4-aminobutyl)imidazole yields 1-nitro-2-[2-((3-methoxy-2-pyridyl)- methylsulphinyl)ethylamino]-2-[4-(4-imidazolyl)-butylamino]ethylene.

EXAMPLE 6

Oxidation of 5-methyl-4-(2-aminoethylthio)methylimidazole with one equivalent of sodium metaperiodate yields 5-methyl-4-(2-aminoethylsulphinyl)methylimidazole and reaction of this compound with carbon disulphide gives N-[2-((5-methyl-4-imidazolyl)methylsulphinyl)ethyl]dithiocarbamic acid which, on treatment with methyl iodide may be converted into S-methyl-N-[2-((5-methyl-4-imidazolyl)methylsulphinyl) ethyl]dithiocarbamate hydriodide.

Reaction of the latter compound with 5-methyl-4-(2-aminoethylthio)methylimidazole results in the production of N-[2-((5-methyl-4-imidazolyl)methylsulphinyl)ethyl]-N'-[2-((5-methyl-4-imidazolyl)methylthio)ethyl]-thiourea.

EXAMPLE 7

Pharmaceutical composition:

| | |
|---|---|
| 1-Nitro-2-[2-(2-thiazolylmethylthio)ethylamino]-2-[2-(2-thiazolylmethylsulphinyl)ethylamino]ethylene | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 8

Pharmaceutical composition:

| | |
|---|---|
| 1-Nitro-2-[2-(2-thiazolylmethylthio)ethylamino]-2-[2-(2-thiazolylmethylsulphinyl)ethylamino]ethylene | 200 mg |
| Lactose | 100 mg |

The ingredients are screened, mixed and filled into a hard gelatin capsule.

What is claimed is:
1. A compound of the formula:

wherein Het and Het' are each selected from imidazole optionally substituted by methyl or bromo and pyridine optionally substituted by methoxy, hydroxy, chlorine or bromine or when one of Het and Het' is pyridine optionally substituted by methoxy, hydroxy, chlorine or bromine, the other of Het or Het' may be selected from thiazole and isothiazole; Z is sulphur, SO or methylene; X is sulphur, CHNO$_2$ or NCN.

2. A compound according to claim 1 wherein Het and Het' are each selected from 5-methyl-4-imidazolyl, 5-bromo-4-imidazolyl, 3-methoxy-2-pyridyl, 3-hydroxy-2-pyridyl, 3-chloro-2-pyridyl and 3-bromo-2-pyridyl or when one of Het or Het' is 3-methoxy-2-pyridyl, 3-hydroxy-2-pyridyl, 3-chloro-2-pyridyl or 3-bromo-2-pyridyl, the other of Het or Het' may be selected from 2-thiazolyl and 3-isothiazolyl.

3. A compound of claim 1 wherein Het and Het' are identical.

4. A compound of claim 1 wherein Z is sulphur or methylene.

5. A compound of claim 1 wherein Z is sulphur.

6. A compound of claim 1 wherein X is CHNO$_2$ or NCN.

7. A pharmaceutical composition for oral administration to block histamine H$_2$-receptors comprising in an amount effective to block said receptors a compound of claim 1 in combination with a pharmaceutically acceptable diluent or carrier.

8. A pharmaceutical composition to block histamine H$_2$-receptors comprising in an amount effective to block said receptors a compound of claim 4 in combination with a pharmaceutically acceptable diluent or carrier.

9. A method of blocking histamine H$_2$-receptors which comprises administering to an animal in an amount effective to block said receptors a compound of claim 1.

10. A compound of claim 1, said compound being N-cyano-N'-[2-((5-methyl-4-imidazolyl)methylthio)ethyl]-N''-[2-((5-methyl-4-imidazolyl)methylsulphinyl)ethyl]guanidine.

* * * * *

UNITED STATES PATENT AND TRADEMARK OFFICE
CERTIFICATE OF CORRECTION

PATENT NO. : 4,105,770

DATED : August 8, 1978

INVENTOR(S) : Graham John Durant, Charon Robin Ganellin, Torben Hesselbo and George Raymond White It is certified that error appears in the above-identified patent and that said Letters Patent are hereby corrected as shown below:

Column 1, line 7, after 4,038,408 , "filed" should read -- issued -- .

Column 4, line 32, after substituting , "and" should read -- an -- .

Signed and Sealed this

Twentieth Day of February 1979

[SEAL]

Attest:

RUTH C. MASON
Attesting Officer

DONALD W. BANNER
Commissioner of Patents and Trademarks